United States Patent [19]
Matassa et al.

[11] Patent Number: 5,552,402
[45] Date of Patent: Sep. 3, 1996

[54] FIVE-MEMBERED HETEROAROMATIC COMPOUNDS AS 5-HT RECEPTOR AGONISTS

[75] Inventors: V. G. Matassa, Rome, Italy; L. J. Street, Harlow; G. A. Showell, Welwyn Garden City, both of England

[73] Assignee: Merck, Sharp & Dohme Ltd., Hoddesdon, England

[21] Appl. No.: 443,615

[22] Filed: May 18, 1995

[30] Foreign Application Priority Data

Jun. 19, 1994 [GB] United Kingdom .................. 9410027
Aug. 4, 1994 [GB] United Kingdom .................. 9415745

[51] Int. Cl.$^6$ ...................... A61K 31/495; A61K 31/535; C07D 401/14; C07D 413/14
[52] U.S. Cl. ...................... 514/233.5; 514/253; 514/339; 544/132; 544/366; 544/62; 546/268.4; 546/268.7; 546/269.1; 546/269.7; 546/271.1; 546/271.4; 546/272.1; 546/272.4; 546/27; 546/275.7; 546/276.4; 546/272.7; 546/277.4; 546/280.4; 546/284.1; 546/281.1

[58] Field of Search ................... 544/132, 366; 546/273; 514/233.5

[56] References Cited

U.S. PATENT DOCUMENTS 5,002,948  3/1991  Perregaard et al. .................. 544/366

FOREIGN PATENT DOCUMENTS

| | | |
|---|---|---|
| 0438230A2 | 7/1991 | European Pat. Off. . |
| 0497512A2 | 5/1992 | European Pat. Off. . |
| 0494774A1 | 7/1992 | European Pat. Off. . |
| 0548813A1 | 6/1993 | European Pat. Off. . |
| WO/93/18029 | 9/1993 | WIPO . |
| WO/94/03446 | 2/1994 | WIPO . |
| WO/94/02477 | 3/1994 | WIPO . |

*Primary Examiner*—Robert W. Ramsuer
*Attorney, Agent, or Firm*—Robert J. North; Melvin Winokur

[57] ABSTRACT

A class of substituted five-membered heteroaromatic compounds are selective agonists of 5-HT$_1$-like receptors and are therefore useful in the treatment of clinical conditions, in particular migraine and associated disorders, for which a selective agonist of these receptors is indicated.

7 Claims, No Drawings

FIVE-MEMBERED HETEROAROMATIC COMPOUNDS AS 5-HT RECEPTOR AGONISTS

The present invention relates to a class of substituted five-membered heteroaromatic compounds which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

Several distinct classes of substituted five-membered heteroaromatic compounds are described in published European patent applications 0438230, 0497512 and 0494774, and published International patent applications 93/18029, 94/02477 and 94/03446. The compounds described therein are stated to be selective agonists of 5-HT$_1$-like receptors, and accordingly to be of particular use in the treatment of migraine and associated conditions. None of these publications, however, discloses nor even suggests the particular substituted five-membered heteroaromatic compounds provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of removing the alkoxypyridine or alkoxypyrimidine substituent, or of replacing it with a simple alkyl substituent; nor is there any suggestion therein that the range of substituents specified at the 5-position of the indole moiety might be successfully replaced by an optionally substituted five-membered heteroaromatic ring.

The present invention provides a compound of formula I, or a salt or prodrug thereof:

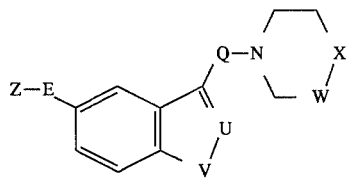

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms;

W represents a methylene group and X represents oxygen, sulphur, N—R$^1$ or CH—R$^1$; or —W—X— represents —CH=C(R$^1$)—;

U represents nitrogen or C—R$^2$;

V represents oxygen, sulphur or N—R$^3$; and

R$^1$, R$^2$ and R$^3$ independently represent hydrogen or C$_{1-6}$ alkyl.

The present invention also provides compounds of formula I above wherein W represents a methylene group and X represents oxygen, sulphur or N—R$^1$; and Z, E, Q, U, V and R$^1$ are as defined above.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "C$_{1-6}$ alkoxy", "C$_{1-6}$ alkylthio" and "C$_{1-6}$ alkylamino" are to be construed accordingly.

The expression "C$_{2-6}$ alkenyl" as used herein refers to straight-chained and branched alkenyl groups containing from 2 to 6 carbon atoms. Typical examples include vinyl and allyl groups.

The expression "C$_{2-6}$ alkynyl" as used herein refers to straight-chained and branched alkynyl groups containing from 2 to 6 carbon atoms. Typical examples include ethynyl and propargyl groups.

Typical C$_{3-7}$ cycloalkyl groups include cyclopropyl, cyclobutyl, cyclopentyl and cyclohexyl.

Typical aryl groups include phenyl and naphthyl.

Particular aryl(C$_{1-6}$)alkyl groups include benzyl, phenethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl(C$_{1-6}$)alkyl groups include pyridylmethyl and pyrazinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E and Q, which may be the same or different, represent straight or branched alkylene chains, these may be, for example, methylene, ethylene, 1-methylethylene, propylene, 2-methylpropylene or butylene. In addition, E may represent a chemical bond such that the moiety Z is attached directly to the benzo moiety of the central fused bicyclic heteroaromatic ring system.

The compound of formula I in accordance with the present invention is suitably an indole, benzofuran or benzthiophene derivative of formula IA, or an indazole derivative of formula IB:

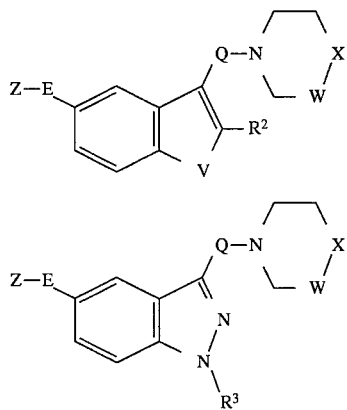

wherein Z, E, Q, W, X, V, $R^2$ and $R^3$ are as defined above. Preferably, the compounds according to the invention are indole derivatives of formula IC:

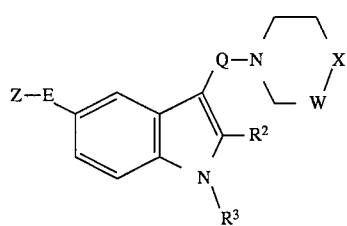

wherein Z, E, Q, W, X, $R^2$ and $R^3$ are as defined above, in particular wherein $R^2$ and $R^3$ are both hydrogen.

Suitably, W represents a methylene group and the moiety X represents oxygen, N—H or N-methyl; or —W—X— represents —CH=CH—.

Suitably, $R^1$, $R^2$ and $R^3$ independently represent hydrogen or methyl, especially hydrogen.

A particular sub-class of compounds according to the invention is represented by the compounds of formula IIA, and salts and prodrugs thereof:

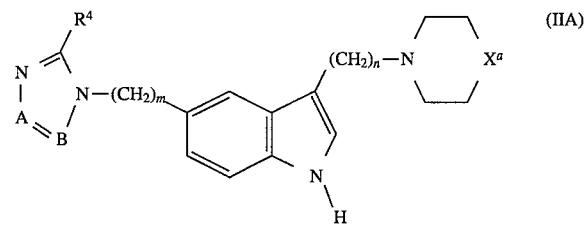

wherein $X^a$ represents oxygen, sulphur or N—$R^1$, in which $R^1$ is as defined with reference to formula I above;

m is zero, 1, 2 or 3;

n is 2, 3, 4 or 5;

A represents nitrogen or CH;

B represents nitrogen or C—$R^5$; and $R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl.

Suitable values of $X^a$ with reference to formula IIA above include oxygen, N—H and N-methyl.

Particular values of $R^4$ and $R^5$ include hydrogen, methyl, ethyl, benzyl and amino, especially hydrogen.

Another sub-class of compounds according to the invention is represented by the compounds of formula IIB, and salts and prodrugs thereof:

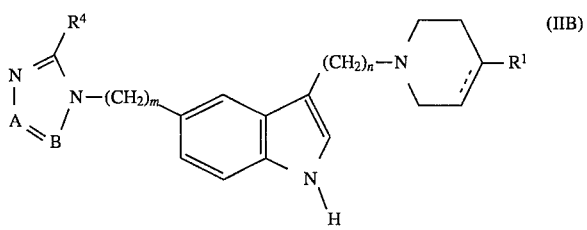

wherein the broken line represents an optional chemical bond;

$R^1$ is as defined with reference to formula I above; and m, n, A, B and $R^4$ are as defined with reference to formula IIA above.

Specific compounds within the scope of the present invention include:

1-[2-(5-(1,2,4-triazol-4-yl)-1H-indol-3-yl)ethyl]-4H-piperazine;

1-[2-(5-(1,2,4-triazol-4-yl)-1H-indol-3-yl)ethyl]-4-methylpiperazine;

4-[2-(5-(1,2,4-triazol-4-yl)-1H-indol-3-yl)ethyl]morpholine;

1-[3-(5-(1,2,4-triazol-4-yl)-1H-indol-3-yl)propyl]-4H-piperazine;

1-[3-(5-(1,2,4-triazol-4-yl)-1H-indol-3-yl)propyl]-4-methylpiperazine;

1-[4-(5-(1,2,4-triazol-4-yl)-1H-indol-3-yl)butyl]-4-methylpiperazine;

1-[2-(5-(1,2,4-triazol-4-yl)-1H-indol-3-yl)ethyl]-1,2,5,6-tetrahydropyridine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein W represents a methylene group, X represents N—R$^1$ and R$^1$ is other than hydrogen may be prepared by a process which comprises N-alkylation of a compound of formula III:

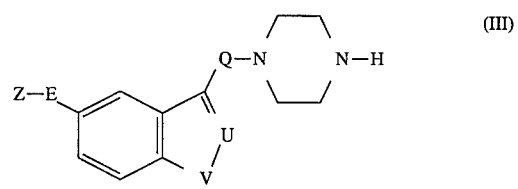

wherein Z, E, Q, U and V are as defined above.

Attachment of the R$^1$ moiety to the compounds of formula III may conveniently be effected by standard alkylation techniques, for example by treatment with a C$_{1-6}$ alkyl halide such as methyl iodide, typically under basic conditions, e.g. sodium hydride in N,N-dimethylformamide, or triethylamine in acetonitrile. Alternatively, the R$^1$ moiety may conveniently be attached by a reductive alkylation procedure, which comprises treating the required compound of formula III as defined above with the appropriate aldehyde, e.g. formaldehyde or acetaldehyde, in the presence of a reducing agent such as sodium cyanoborohydride.

The compounds of formula III above wherein U represents C—R$^2$ and V represents N—R$^3$, corresponding to the indole derivatives of formula IC as defined above wherein W represents a methylene group and X represents N—H, may be prepared by a process which comprises reacting a compound of formula IV:

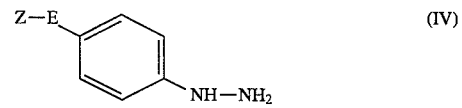

wherein Z and E are as defined above; with a compound of formula V, or a carbonyl-protected form thereof:

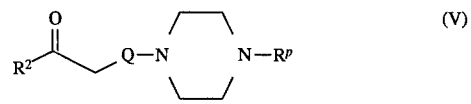

wherein R$^2$ and Q are as defined above, and R$^p$ represents an amino-protecting group; followed, where required, by N-alkylation by standard methods to introduce the moiety R$^3$; with subsequent removal of the amino-protecting group R$^p$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group R$^p$ in the compounds of formula V is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

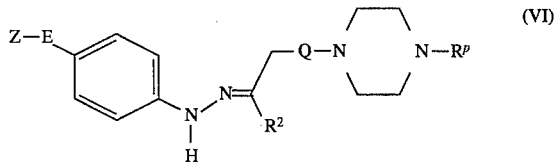

wherein Z, E, Q, $R^2$ and $R^p$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

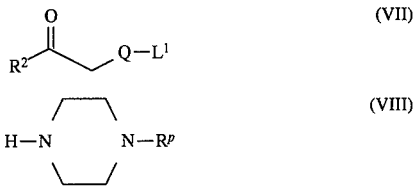

wherein Q, $R^2$ and $R^p$ are as defined above, and $L^1$ represents a suitable leaving group.

The leaving group $L^1$ is suitably a halogen atom, e.g. chlorine or bromine.

Where $L^1$ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein U represents $C-R^2$, V represents $N-R^3$ and X is other than N—H—i.e. the indole derivatives of formula IC as defined above wherein W represents a methylene group and X represents oxygen, sulphur, $N-(C_{1-6})$alkyl or $CH-R^1$, or $-W-X-$ represents $-CH=C(R^1)-$, in which $R^1$ is as defined above—may be prepared by a process which comprises reacting a compound of formula IV as defined above with a compound of formula IX, or a carbonyl-protected form thereof:

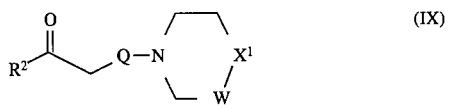 (IX)

wherein Q and $R^2$ are as defined above; W represents a methylene group and $X^1$ represents oxygen, sulphur or $N-R^{11}$ in which $R^{11}$ represents $C_{1-6}$ alkyl; or $-W-X^1-$ represents $-CH=C(R^1)-$ in which $R^1$ is as defined above; under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula IX include the dimethyl acetal or ketal derivatives.

As with that between compounds IV and V, the Fischer reaction between compounds IV and IX may be carried out in a single step, or may proceed via an initial non-cyclising step at a lower temperature to give an intermediate of formula X:

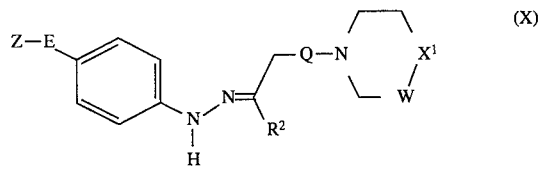 (X)

wherein Z, E, Q, $R^2$, W and $X^1$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

 (XI)

wherein W and $X^1$ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

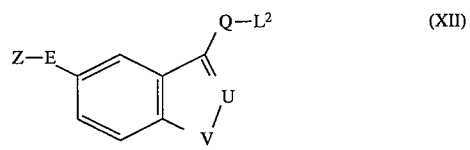 (XII)

wherein Z, E, Q, U and V are as defined above, and $L^2$ represents a suitable leaving group; followed by removal of the amino-protecting group $R^p$.

Similarly, the compounds of formula I wherein X is other than N—H may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, typically in the presence of a base such as sodium carbonate or potassium carbonate, optionally with the addition of a catalytic amount of sodium iodide.

In a representative embodiment, the compounds of formula XII wherein U represents CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating an acid addition salt of the hydrazine derivative IV, typically the hydrochloride salt, in an inert solvent such as dioxan, at the reflux temperature of the solvent.

In a further procedure, the compounds of formula III above wherein U represents nitrogen and V represents $N-R^3$, corresponding to the indazole derivatives of formula IB as defined above wherein W represents a methylene group and X represents N—H, may be prepared by a process which comprises cyclising a compound of formula XIII:

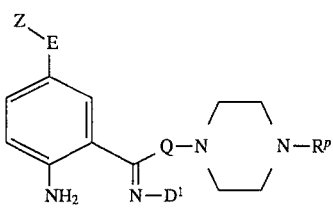

(XIII)

wherein Z, E, Q and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein U represents nitrogen, V represents N—$R^3$ and X is other than N—H may be prepared by a process which comprises cyclising a compound of formula XIV:

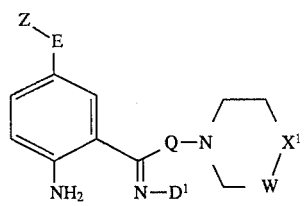

(XIV)

in which Z, E, Q, W, $X^1$ and $D^1$ are as defined above.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

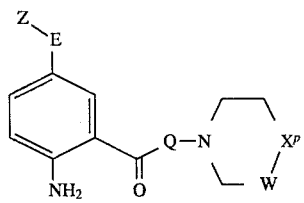

(XV)

wherein Z, E and Q are as defined above, and —W—$X^p$— corresponds to the moiety —W—$X^1$— as defined above or represents —$CH_2$—N($R^p$)— in which $R^p$ is as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XV may conveniently be prepared by ozonolysis of the corresponding indole derivative of formula XVI:

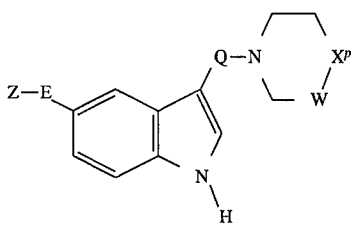

(XVI)

wherein Z, E, Q, W and $X^p$ are as defined above; followed by a reductive work-up, advantageously using dimethylsulphide.

The indole derivatives of formula XVI may be prepared by methods analogous to those described in the accompanying Examples, or by procedures well known from the art.

In a still further procedure, the compounds of formula III above wherein U represents C—$R^2$ and V represents oxygen or sulphur, corresponding to the benzofuran or benzthiophene derivatives of formula IA wherein V is oxygen or sulphur respectively, W represents a methylene group and X represents N—H, may be prepared by a process which comprises cyclising a compound of formula XVII:

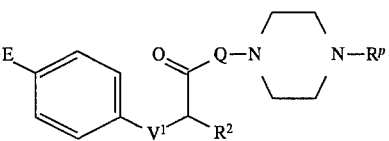

(XVII)

wherein Z, E, Q, $R^2$ and $R^p$ are as defined above, and $V^1$ represents oxygen or sulphur; followed by removal of the amino-protecting group $R^p$.

Similarly, the compounds of formula I wherein U represents C—$R^2$, V represents oxygen or sulphur and X is other than N—H may be prepared by a process which comprises cyclising a compound of formula XVIII:

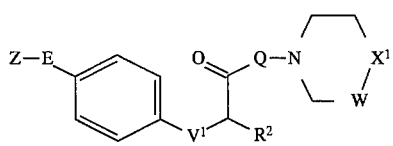

(XVIII)

wherein Z, E, Q, $R^2$, $V^1$, W and $X^1$ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

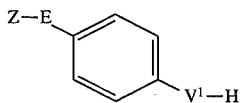

(XIX)

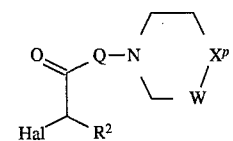

(XX)

wherein Z, E, Q, $R^2$, $V^1$, W and $X^p$ are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

The hydrazine derivatives of formula IV above may be prepared by methods analogous to those described in EP-A-0438230 and EP-A-0497512.

Where they are not commercially available, the starting materials of formula VII, VIII, XI and XX may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. Indeed, as will be appreciated, the compounds of formula III above are compounds according to the invention in their own right. In particular, a compound of formula I wherein —W—X— represents —CH=C($R^1$)— initially obtained may be readily converted into the corresponding compound wherein —W—X— represents —$CH_2$—CH($R^1$)— by conventional catalytic hydrogenation procedures. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The activity of test compounds as agonists of the 5-$HT_1$-like receptor was measured in terms of their ability to mediate contraction of the saphenous vein of New Zealand White rabbits, using the procedure described in *Arch. Pharm.*, 1990, 342, 111. Agonist potencies were calculated as $EC_{50}$ values, from plots of percentage 5-HT (1 μM) response against the concentration of the agonist. The compounds of accompanying Examples 4 and 5 were tested in this assay and were found to possess $EC_{50}$ values of less than 5.0 μM.

EXAMPLE 1

1-(2-[5-(1,2,4-Triazol-4-yl)-1H-indol-3-yl]ethyl)-4-(H))-piperazine, Succinate Hemihydrate 1. Intermediate 1:
4'-(1,2,4-Triazol-4-yl)phenylhydrazine a) 4'-Aminoacetanilide A solution of 4-nitroacetanilide (5.0 g, 27.8 mmol) in EtOH/EtOAc (160 ml, 1:1), $H_2O$ (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in $H_2O$, basifying with 2N NaOH and extracting into EtOAc. The combined extracts were dried ($MgSO_4$) and evaporated to give the title-aniline (3.75 g, 90%). δ (250 MHz, $CDCl_3$/$d_4$-MeOH) 2.10 (3H, s, Me); 6.68 (2H, d, J=8.8 Hz, Ar—H); 7.27 (2H, d, J=8.8 Hz, Ar—H).

b) 4'-(1,2,4-Triazol-4-yl)acetanilide

A mixture of the preceding aniline (3.52 g, 23.4 mmol), N,N-dimethylformamide azine (3.33 g, 23.4 mmol; *J. Chem. Soc.* (C), 1967, 1664) and p-toluenesulphonic acid monohydrate (0.223 g, 1.17 mmol), in anhydrous toluene (100 ml) was heated at reflux for 17 h. The beige coloured precipitate was filtered off and washed with toluene and $CH_2Cl_2$ and dried under vacuum to give the desired triazole (4.29 g, 91%); δ (250 MHz, $d_4$-MeOH/$d_6$-DMSO) 2.14 (3H, s, $CH_3$); 7.60 (2H, d, J=8.8 Hz, Ar—H); 7.78 (2H, d, J=8.8 Hz, Ar—H); 8.96 (2H, s, Ar—H).

c) 4'-(1,2,4-Triazol-4-yl)phenylaniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with $CH_2Cl_2$ (×5). The combined extracts were dried ($MgSO_4$) and evaporated and the residue chromatographed on silica gel, eluting with $CH_2Cl_2$/MeOH/$NH_3$ (80:8:1), to give the title-aniline (2.94 g, 76%); δ (250 MHz, $CDCl_{13}$) 3.80 (2H, s, $NH_2$); 6.71 (2H, d, J=8.8 Hz, Ar—H); 7.08 (2H, d, J=8.8 Hz, Ar—H); 8.36 (2H, s, Ar—H).

d) 4'-(1,2,4-Triazol-4-yl)phenylhydrazine

To a solution of the preceding aniline (1.60 g, 9.99 mmol) in concentrated HCl/$H_2O$ (23 ml and 3 ml respectively) was added, at −21° C., a solution of $NaNO_2$ (0.69 g, 9.99 mmol) in $H_2O$ (8 ml), at such a rate as to maintain the temperature below −10° C. The mixture was stirred for 0.3 h and then filtered rapidly through a sinter, under vacuum. The filtrate was added to a cooled (−20° C.) solution of $SnCl_2.2H_2O$ (9.02 g, 40.0 mmol) in concentrated HCl (17 ml). The mixture was stirred at −20° C. for 0.25 h and then at room temperature for 1.25 h. The resulting solid was filtered off, washed with $Et_2O$ and dried under vacuum. The crude product was dissolved in $H_2O$, basified with concentrated aqueous NaOH and extracted with EtOAc (×5). The combined extracts were dried ($MgSO_4$) and evaporated to afford the title-product (0.95 g, 54%); δ (250 MHz, $CDCl_3$/$d_4$-MeOH) 3.98 (3H, br s, NH and $NH_2$); 6.97 (2H, d, J=12.0 Hz, Ar—H); 7.25 (2H, d, J=12.0 Hz, Ar—H); 8.48 (2H, s, Ar—H).

2. Intermediate 2:
4-(4-tert-Butyloxycarbonyl)piperazin-1-yl Butanal Dimethyl Acetal A mixture of 4-chlorobutanal dimethyl acetal (*J. Chem. Soc., Perkin Trans.* 1, 1981, 251–255; 4.1 g, 26.9 mmol), $K_2CO_3$ (4.08 g, 29.6 mmol) and tert-butyl-1-piperazinecarboxylate (5.00 g, 26.9 mmol), in anhydrous DMF (100 ml) was heated at 100° C. for 24 h. The mixture was cooled to room temperature, water (75 ml) added and extracted with ethyl acetate (5×100 ml). The combined extracts were washed with water (×3), dried ($Na_2SO_4$) and evaporated. The crude product was chromatographed on silica gel eluting with ethyl acetate to give the title-product (3.41 g, 42%). δ (250 MHz, $CDCl_3$) 1.46 (9H, s, $OC(Me)_3$); 1.50–1.68 (4H, m, 2 of $CH_2$); 2.32–2.42 (6H, m, 3 of $CH_2$); 3.30 (6H, s, $(OMe)_2$); 3.40–3.48 (4H, m, 2 of $CH_2$); 4.38 (1H, t, J=6 Hz, C$\underline{H}$).

3. 1-(2-[5-(1,2,4-Triazol-4-yl)-1H-indol-3-yl]ethyl)-4-(H)-piperazine, Succinate Hemihydrate A mixture of intermediates 1 (1.0 g, 5.71 mmol) and 2 (2.07 g, 6.86 mmol) in 4% sulphuric acid (30 ml) was heated at reflux for 48 h. The solution was cooled in an ice-bath, basified with solid $K_2CO_3$ and extracted with butan-1-ol (×3). The solvent was removed under vacuum and azeotroped with hexane (×2). The crude product was chromatographed through silica gel eluting with $CH_2Cl_2$/MeOH/$NH_3$ (30:8:1) to give the title-indole (282 mg, 17%). The succinate hemihydrate salt was prepared: mp 227°–228° C. (Found: C, 59.11; H, 6.58; N, 22.54.

$C_{16}H_{20}N_6.0.5(C_4H_6O_4).0.65H_2O$ requires C, 58.89; H, 6.67; N, 22.89%); δ (360 MHz, $D_2O$) 2.39 (2H, s, succinate); 2.78–2.96 (8H, m, 4 of $CH_2$); 3.25–3.27 (4H, m, 2 of $CH_2$); 7.19 (1H, dd, J=2.0 and 8.6 Hz, Ar—H); 7.29 (1H, s, Ar—H); 7.51 (1H, d, J=8.6 Hz, Ar—H); 7.59 (1H, d, J=2.0 Hz, Ar—H); 8.90 (2H, s, Triazole-H).

EXAMPLE 2

1-(2-[5-(1,2,4-Triazol-4-yl)-1H-indol-3-yl]ethyl)-4-(methyl)piperazine. 3.5 Hydrogen Oxalate Monohydrate A solution of formaldehyde (38% w/v solution in $H_2O$; 63 mg; 0.81 mmol) in methanol (5 ml) was added dropwise to a stirred solution of Example 1 (0.20 g, 0.67 mmol), acetic acid (0.10 g, 1.7 mmol) and sodium cyanoborohydride (51 mg, 0.81 mmol) in methanol (25 ml), at +5° C. The solution was warmed to room temperature and stirred for 2 h. The mixture was basified with sat. $K_2CO_3$ solution, the solvent removed under vacuum and the residue extracted with EtOAc (3×). The combined extracts were dried ($Na_2SO_4$), evaporated, and the crude product purified by flash chromatography on silica gel eluting with $CH_2Cl_2$/MeOH/$NH_3$ (60:8:1) to give the title-N-methylpiperazine (0.137 g, 66%). The trihydrogen oxalate monohydrate salt was prepared: mp 226°–228° C.

(Found: C, 44.64; H, 4.81; N, 12.83.$C_{17}H_{22}N_6.3.5(C_2H_2O_4).H_2O$ requires C, 44.79; H, 4.86; N, 13.06%); δ (360 MHz, $D_2O$) 3.00 (3H, s, Me); 3.30 (2H, t, J=7.3 Hz, $CH_2$); 3.38–4.00 (10H, m, 5 of $CH_2$); 7.36 (1H, dd, J=1.9 and 8.7Hz, Ar—H); 7.45 (1H, s, Ar—H); 7.64 (1H, d, J=8.7 Hz, Ar—H); 7.82 (1H, d, J=1.9 Hz, Ar—H); 9.33 (2H, s, Triazole-H).

EXAMPLE 3

4-(2-[5-(1,2,4-Triazol-4-yl)-1H-indol-3-yl]ethyl)morpholine. Hydrogen Oxalate. Hemihydrate 1. Intermediate 3: 4-(Morpholin-4-yl) Butanal Dimethyl Acetal A mixture of 4-chlorobutanal dimethyl acetal (10.0 g, 65.5 mmol) and morpholine (39.96 g, 0.46 mol) was heated at 100° C. for 16 h. The morpholine was then removed under vacuum and water (70 ml) and EtOAc (100 ml) added to the residue. The aqueous layer was separated and extracted further with EtOAc (×3). The combined extracts were dried ($Na_2SO_4$) and evaporated and the residue distilled under vacuum (bp: 104° C. at 2.5 mmHg) to give the title-acetal (10.33 g, 78%). δ (250 MHz, $CDCl_3$) 1.60–1.82 (4H, m, 2 of $CH_2$); 2.44–2.60 (6H, m, 3 of $CH_2$); 3.46 (6H, s, $(OMe)_2$); 3.78–3.84 (4H, m, 2 of $CH_2$); 4.60 (1H, t, J=6 Hz, CH).

2. 4-(2-[5-(1,2,4-Triazol-4-yl)-1H-indol-3-yl]ethyl)morpholine. Hydrogen Oxalate. Hemihydrate A mixture of intermediate 1 (0.50 g, 2.85 mmol) and intermediate 3 (0.58 g, 2.85 mmol) in 4% sulphuric acid (25 ml) was heated at reflux for 21 h. The solution was cooled in an ice-bath, basified with sat. $K_2CO_3$ solution and extracted with EtOAc (2×150 ml). The combined extracts were dried ($Na_2SO_4$), evaporated, and the crude product chromatographed on silica gel eluting with $CH_2Cl_2$/MeOH/$NH_3$ (40:8:1) to give the title-indole (0.16 g, 19%). The hydrogen oxalate hemihydrate salt was prepared: mp 130° C.; (Found: C, 54.41; H, 5.69; N, 17.58.

$C_{16}H_{19}N_5O.C_2H_2O_4.0.5H_2O$ requires C, 54.54; H, 5.59; N, 17.67%); m/e 298 (M+1)$^+$; δ (360 MHz, $D_2O$) 3.22–3.27 (4H, m, 2 of $CH_2$); 3.48–3.60 (4H, m, 2 of $CH_2$); 3.74–3.88 (2H, m, $CH_2$); 4.06–4.26 (2H, m, $CH_2$); 7.30 (1H, dd, J=2.0 and 8.6 Hz, Ar—H); 7.41 (1H, s, Ar—H); 7.60 (1H, d, J=8.6 Hz, Ar—H); 7.72 (1H, d, J=2.0 Hz, Ar—H); 8.81 (2H, s, Triazole-H).

EXAMPLE 4

1-(3-[5-(1,2,4-Triazol-4-yl)-1H-indol-3-yl]propyl)-4-(H)-piperazine. 3.5 Hydrogen Oxalate 1. Intermediate 4: 5-(4-tert-Butyloxycarbonyl)piperazin-1-yl Pentanal Dimethyl Acetal a) 5-Bromopentanal Dimethyl Acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mmol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine, dried ($Na_2SO_4$) and evaporated. The crude product was chromatographed on silica gel eluting with diethyl ether/hexane (1:9) to give the title-acetal (27.5 g, 57%). δ (250 MHz, $CDCl_3$) 1.43–1.67 (4H, m, 2 of $CH_2$); 1.83–1.94 (2H, m, $CH_2$); 3.38 (6H, s, $CH(OMe)_2$); 3.42 (2H, t, J=7 Hz, $CH_2Br$), 4.37 (1H, t, J=7 Hz, C$\underline{H}(OMe)_2$).

b) 5-(4-tert-Butyloxycarbonyl)piperazin-1-yl Pentanal Dimethyl Acetal

A mixture of 5-bromovaleraldehyde dimethyl acetal (27.5 g, 0.13 mmol), $Na_2CO_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250 MHz, $CDCl_3$) 1.29–1.71 (6H, m, 3 of $CH_2$); 1.46 (9H, s, $OC(Me)_3$); 2.31–2.39 (6H, m, 3 of $CH_2$); 3.32 (6H, s, $CH(OMe)_2$); 3.41–3.45 (4H, m, 2 of $CH_2$); 4.36 (1H, t, J=6 Hz, $CH(OMe)_2$).

2.
1-(3-[5-(1,2,4-Triazol-4-yl)-1H-indol-3-yl]propyl)-4-(H)-piperazine. 3.5 Hydrogen Oxalate Prepared from intermediates 1 (5.0 g, 28.6 mmol) and 4 (9.03 g, 28.6 mmol) using the procedure described for Example 1. The crude product was purified by chromatography on silica gel eluting with $CH_2Cl_2$/MeOH/$NH_3$ (30:8:1) to give the title-indole (3.9 g, 44%). The 3.5 hydrogen oxalate salt was prepared using 200 mg of free base: mp 90°–92° C.

(Found: C, 45.97; H, 4.76; N, 13.77. $C_{17}H_{22}N_6$·3.5($C_2H_2O_4$) requires C, 46.08; H, 4.76; N, 13.43%); δ (360 MHz, $D_2O$) 2.12–2.24 (2H, m, $CH_2$); 2.93 (2H, t, J=7 Hz, $CH_2$); 3.46–3.76 (8H, m, 4 of $CH_2$); 7.37 (1H, dd, J=1.9 and 8.7 Hz, Ar—H); 7.39 (1H, s, Ar—H); 7.66 (1H, d, J=8.7, Ar—H); 7.82 (1H, d, J=1.9 Hz, Ar—H); 9.13 (2H, s, Triazole-H).

EXAMPLE 5

1-(3-[5-(1,2,4-Triazol-4-yl)-1H-indol-3-yl]propyl)-4-(methyl)piperazine. 3.5 Hydrogen Oxalate Monohydrate The title-compound was prepared from Example 4 using the procedure described for Example 2. The 3.5 hydrogen oxalate monohydrate salt was prepared: mp 178°–180° C. (Found: C, 45.41; H, 4.86; N, 12.97. $C_{18}H_{24}N_6$·3.5($C_2H_2O_4$)·$H_2O$ requires C, 45.66; H, 5.05; N, 12.78%); δ (360 MHz, $D_2O$) 2.08–2.20 (2H, m, $CH_2$); 2.89 (2H, t, J=6.7 Hz, $CH_2$); 2.99 (3H, s, Me); 3.26–3.33 (2H, m, $CH_2$); 3.38–3.96 (8H, m, 4 of $CH_2$); 7.35 (1H, d, J=8.7 Hz, Ar—H); 7.36 (1H, s, Ar—H); 7.63 (1H, d, J=8.7 Hz, Ar—H); 7.80 (1H, s, Ar—H); 9.26 (2H, s, Triazole-H).

EXAMPLE 6

1-(4-[5-(1,2,4-Triazol-4-yl)-1H-indol-3-yl]butyl)-4-(methyl)piperazine. 1.6 Hydrogen Oxalate. 0.75 Hydrate 1. Intermediate 5:
6-(4-tert-Butoxycarbonyl)piperazin1-yl Hexanal Dimethyl Acetal The title-compound was prepared from 6-bromohexanoyl chloride using the procedure described for Intermediate 4. δ (360 MHz, $CDCl_3$) 1.30–1.63 (8H, m, 4 of $CH_2$); 1.46 (9H, s, $OC(Me)_3$); 2.31–2.40 (6H, m, 3 of $CH_2$); 3.31 (6H, s, $CH(OMe)_2$); 3.40–3.46 (4H, m, 2 of $CH_2$); 4.35 (1H, t, J=5.7 Hz, $CH(OMe)_2$).

2. 1-(4-[5-(1,2,4-Triazol-4-yl)-1H-indol-3-yl]butyl)-4-H)-piperazine

A solution of intermediate 1 (1.0 g, 5.71 mmol) and intermediate 5 (1.9 g, 5.76 mmol), in 4% $H_2SO_4$ (100 ml), was heated at reflux for 20 h. The mixture was cooled to room temperature, basified with $K_2CO_3$ and extracted with n-butanol (×4). The crude product remaining after removing the solvent under vacuum, and azeotroping with hexane (× 2), was chromatographed on silica gel eluting with $CH_2Cl_2$/MeOH/$NH_3$ (30:8:1) to give the title-product (0.7 g, 38%). δ (360 MHz, $d_6$-DMSO) 1.44–1.52 (2H, m, $CH_2$); 1.62–1.70 (2H, m, $CH_2$); 2.23–2.27 (6H, m, 3 of $CH_2$); 2.62–2.65 (4H, m, 2 of $CH_2$); 2.71 (2H, t, J=7.4 Hz, $CH_2$); 7.26 (1H, s, Ar—H); 7.29 (1H, dd, J=2.1 and 8.5 Hz, Ar—H); 7.47 (1H, d, J=8.5 Hz, Ar—H); 7.77 (1H, d, J=2.1 Hz, Ar—H); 9.01 (2H, s, Triazole-H); 11.05 (1H, s, NH).

3. 1-(4-[5-(1,2,4-Triazol-4-yl)-1H-indol-3-yl]butyl)-4-(methyl)piperazine. 1.6 Hydrogen Oxalate. 0.75 Hydrate The title compound was prepared from 1-(4-[5-(1,2,4-triazol-4-yl)-1H-indol-3-yl]butyl)-4-(H)-piperazine using the general procedure described for Example 2. The 1.6 hydrogen oxalate 0.75 hydrate salt was prepared: mp 215°–216° C. (Found: C, 53.84; H, 6.30; N, 17.19. $C_{19}H_{26}N_6$·1.6($C_2H_2O_4$)·0.75$H_2O$ requires C, 53.76; H, 6.24; N, 16.94%); m/e 319 (M+1)$^+$; δ (360 MHz, $D_2O$) 1.66–1.82 (4H, m, 2 of $CH_2$); 2.79 (2H, t, J=6.6 Hz, $CH_2$); 2.96 (3H, s, Me); 3.20 (2H, t, J=7.0 Hz, $CH_2$); 3.56 (8H, br s, 4 of $CH_2$); 7.24 (1H, dd, J=2.0 and 8.6 Hz, Ar—H); 7.30 (1H, s, Ar—H); 7.56 (1H, d, J=8.6 Hz, Ar—H); 7.66 (1H, d, J=2.0 Hz, Ar—H); 8.74 (2H, s, Triazole-H).

EXAMPLE 7

1-(2-[5-(1,2,4-Triazol-4-yl)-1H-indol-3-yl]ethyl)-1,2,5,6-tetrahydropyridine, 1.8 Hydrogen Oxalate The title compound was prepared as described in Example 1 from 4'-(1,2,4-triazol-4-yl)phenylhydrazine and 4-(1,2,5,6-tetrahydropyridin-1-yl) butanal dimethylacetal. The hydrogen oxalate salt had mp 123°–5° C. (Found: C, 54.17, H, 5.14, N, 15.03.

$C_{17}H_{19}N_5$·1.8($C_2H_2O_4$) requires C, 54.33, H, 5.00, N, 15.38%), δ (360 MHz, $d_6$-DMSO) 2.34–2.44 (2H, m, 1 of $CH_2$), 3.16–3.22 (2H, m, 1 of $CH_2$), 3.3–3.4 (4H, m, 2 of $CH_2$), 3.75–3.85 (2H, m, 1 of $CH_2$), 5.7–5.8 (1H, m, CH), 5.9–6.0 (1H, m, CH), 7.35 (1H, dd, J=2 Hz, $J_2$=9 Hz, Ar—H), 7.41 (1H, dd, J=2 Hz, Ar—H), 7.53 (1H, d, J=2 Hz, Ar—H), 7.89 (1H, d, J=2 Hz, Ar—H), 9.02 (2H, s, triazole-H), 11.3 (1H, br s indole NH), MS, ES$^+$ m/e for (M+H)$^+$= 294.

What is claimed is:
1. A compound of formula I, or a pharmaceutically acceptable salt or prodrug thereof:

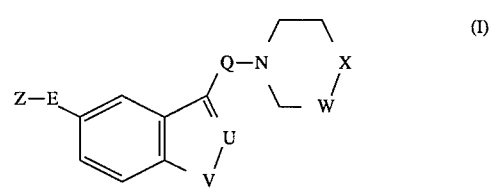

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms;

W represents a methylene group and X represents oxygen, sulphur or N—$R^1$, or —W—X— represents —CH=C($R^1$)—;

U represents nitrogen or C—$R^2$;

V represents oxygen, sulphur or N—$R^3$; and $R^1$, $R^2$ and $R^3$ independently represent hydrogen or $C_{1-6}$ alkyl.

2. A compound as claimed in claim 1 wherein W represents a methylene group and X represents oxygen, sulphur or N—$R^1$, in which $R^1$ is as defined in claim 1.

3. A compound as claimed in claim 1 represented by formula IIA, and salts pharmaceutically acceptable and prodrugs thereof:

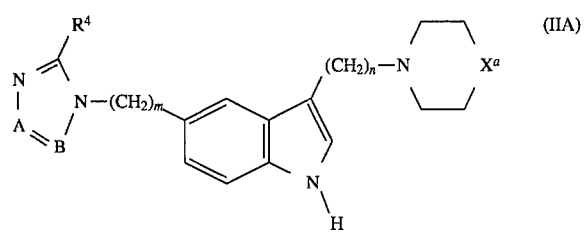

(IIA)

wherein $X^a$ represents oxygen, sulphur or N—$R^1$, in which $R^1$ is as defined in claim 1;

m is zero, 1, 2 or 3;

n is 2, 3, 4 or 5;

A represents nitrogen or CH;

B represents nitrogen or C—$R^5$; and $R^4$ and $R^5$ independently represent hydrogen, $C_{1-6}$ alkyl, $C_{2-6}$ alkenyl, $C_{3-7}$ cycloalkyl, aryl, aryl($C_{1-6}$alkyl, $C_{3-7}$ heterocycloalkyl, heteroaryl, heteroaryl($C_{1-6}$alkyl, $C_{1-6}$ alkoxy, $C_{1-6}$ alkylthio, amino, $C_{1-6}$ alkylamino, di($C_{1-6}$ alkylamino, halogen, cyano or trifluoromethyl.

4. A compound as claimed in claim 1 represented by formula IIB, and salts and prodrugs thereof:

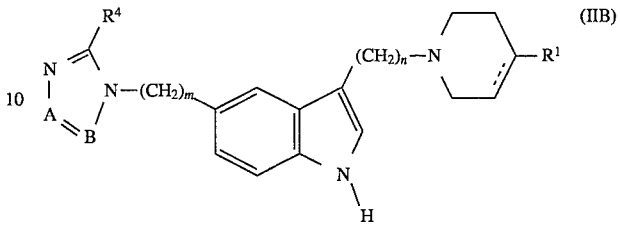

(IIB)

wherein the broken line represents a chemical bond;

$R^1$ is as defined in claim 1; and m, n, A, B and $R^4$ are as defined in claim 3.

5. A compound as claimed in claim 1 selected from:

1-[2-(5-(1,2,4-triazol-4-yl)-1H-indol-3-yl)ethyl]-4H-piperazine;

1-[2-(5-(1,2,4-triazol-4-yl)-1H-indol-3-yl)ethyl]-4-methylpiperazine;

4-[2-(5-(1,2,4-triazol-4-yl)-1H-indol-3-yl)ethyl]morpholine;

1-[3-(5-(1,2,4-triazol-4-yl)-1H-indol-3-yl)propyl]-4H-piperazine;

1-[3-(5-(1,2,4-triazol-4-yl)-1H-indol-3-yl)propyl]-4-methylpiperazine;

1-[4-(5-(1,2,4-triazol-4-yl)-1H-indol-3-yl)butyl]-4-methylpiperazine;

1-[2-(5-(1,2,4-triazol-4-yl)-1H-indol-3-yl)ethyl]-1,2,5,6-tetrahydropyridine;

and pharmaceutically acceptable salts and prodrugs thereof.

6. A pharmaceutical composition comprising a compound as claimed in claim 1 in association with a pharmaceutically acceptable carrier.

7. A method for the treatment and/or prevention of clinical conditions for which a selective agonist of 5-$HT_1$-like receptors is indicated, which comprises administering to a patient in need of such treatment an effective amount of a compound as claimed in claim 1.

* * * * *